(12) United States Patent
Whiteside

(10) Patent No.: US 6,387,066 B1
(45) Date of Patent: May 14, 2002

(54) SELF-ALIGNING ADJUSTABLE ORTHOPEDIC JOINT BRACE

(76) Inventor: Joseph Whiteside, 61 Renwick, Poland, OH (US) 44514

( * ) Notice: Subject to any disclaimer, the term of this patent is extended or adjusted under 35 U.S.C. 154(b) by 23 days.

(21) Appl. No.: 09/684,088

(22) Filed: Oct. 10, 2000

(51) Int. Cl.$^7$ .................................................. A61F 5/00
(52) U.S. Cl. .............................. 602/16; 602/23; 602/26
(58) Field of Search .......................... 602/5, 16, 23, 602/26; 128/846, 869, 882

(56) References Cited

U.S. PATENT DOCUMENTS

| | | | |
|---|---|---|---|
| 4,256,097 A | | 3/1981 | Willis |
| 5,302,169 A | | 4/1994 | Taylor |
| 5,352,190 A | * | 10/1994 | Fischer .................. 602/26 |
| 5,507,719 A | * | 4/1996 | Freemen .................. 602/26 |
| 5,669,873 A | | 9/1997 | Towsley |
| 5,766,140 A | | 6/1998 | Tillinghast, III et al. |
| 6,024,713 A | * | 4/2000 | Barney .................... 602/23 |

OTHER PUBLICATIONS

OA Adjuster—dj ortho—dj orthopedics, L.L.C.

* cited by examiner

Primary Examiner—Michael A. Brown
(74) Attorney, Agent, or Firm—Harpman & Harpman

(57) ABSTRACT

An orthopedic brace having a pair of arm assemblies secured to a human body. A self-aligning polycentric joint interconnecting the arms allow for bending of the knee joint while selectively imparting stress to the joint or angular inclination in a linear fashion. The use of spherical bearings at the joint access combined with selective linear adjustment to the arm assemblies imparts varus/valgus range of angular inclination while allowing the normal extension and flexation of the anatomical joint.

14 Claims, 4 Drawing Sheets

SELF-ALIGNING ADJUSTABLE ORTHOPEDIC JOINT BRACE

BACKGROUND OF THE INVENTION

1. Technical Field

This invention relates to orthopedic braces and supports specifically for the anatomical joints. Such braces address variations in human joints and hold the joint in varying alignments to eliminate discomfort while allowing for use and mobility of the patient.

2. Description of Prior Art

Prior art devices of this type have relied on a variety of different joint support braces and the like to impart stability and allow for joint flexation. Many such prior art orthopedic braces have been developed that use hinges between pairs of upright support arms secured to the wearers upper leg above the knee joint and the lower leg below the knee joint. These devices are used to control flexation and extension range of motion of the joint itself. Others are concerned with the ability to adjust the angle of inclination between the uprights. Such knee braces utilize a single pair of support joint arms can be seen U.S. Pat. No. 5,302,169 wherein a post operative knee brace is disclosed utilizing a pair of arms interconnected by a pivotal joint. Registering bearing plates have slots and engagement bolts to allow for movement therebetween.

In U.S. Pat. No. 4,256,097 a protection and support joint for a knee can be seen wherein a pair of leg engagement cuffs are interconnected by a ball and socket joint that allows for controlled flexation of the knee joint.

A flexible leg brace can be seen in U.S. Pat. No. 5,669,873 wherein a threaded rod adjustably interconnects upper and lower support elements.

An angular compensation device for a joint brace can be seen in U.S. Pa. No. 5,766,140 wherein a joint which has a hinge positioned with a hinge pin and two hinge levers rotate relatively to one another around the pin, with an arch bar and support pins. Movement of the hinge leaves will impart an angular adjustability to the brace in spaced relation to the hinge having interengaging upper and lower rotational gear segments.

An example of a dual upright support arm assembly with an adjustable varus/valgus is seen in the OA Adjuster by dj Orthopedic, LLC of Vista, Calif. for the treatment of uni-compartamental osteoarthritis (see Exhibit 1 brochure attached). This device is designed to stress the anatomical knee joint by allowing lateral input to the joint configuration. This arrangement requires that the angular compensation having been made will move away from the joint head.

SUMMARY OF THE INVENTION

The present invention is directed to an orthopedic brace for anatomical joints. The brace having pairs of support arms secured bilaterally to a wearers body. The support arms are pivotally connected to one another by a self-alignment polycentric joints having multiple spherical bearings. The angle of inclination of the support arms to one another can be adjusted by linearly foreshortening or lengthening the proximal or distal end of the support arms in each pair. The support arms have an inner meshing, interconnected contoured geared surface at their respective distal ends to define the normal bending range of the anatomical joint on which the brace is positioned.

DESCRIPTION OF THE PREFERRED EMBODIMENT

Figure 1:
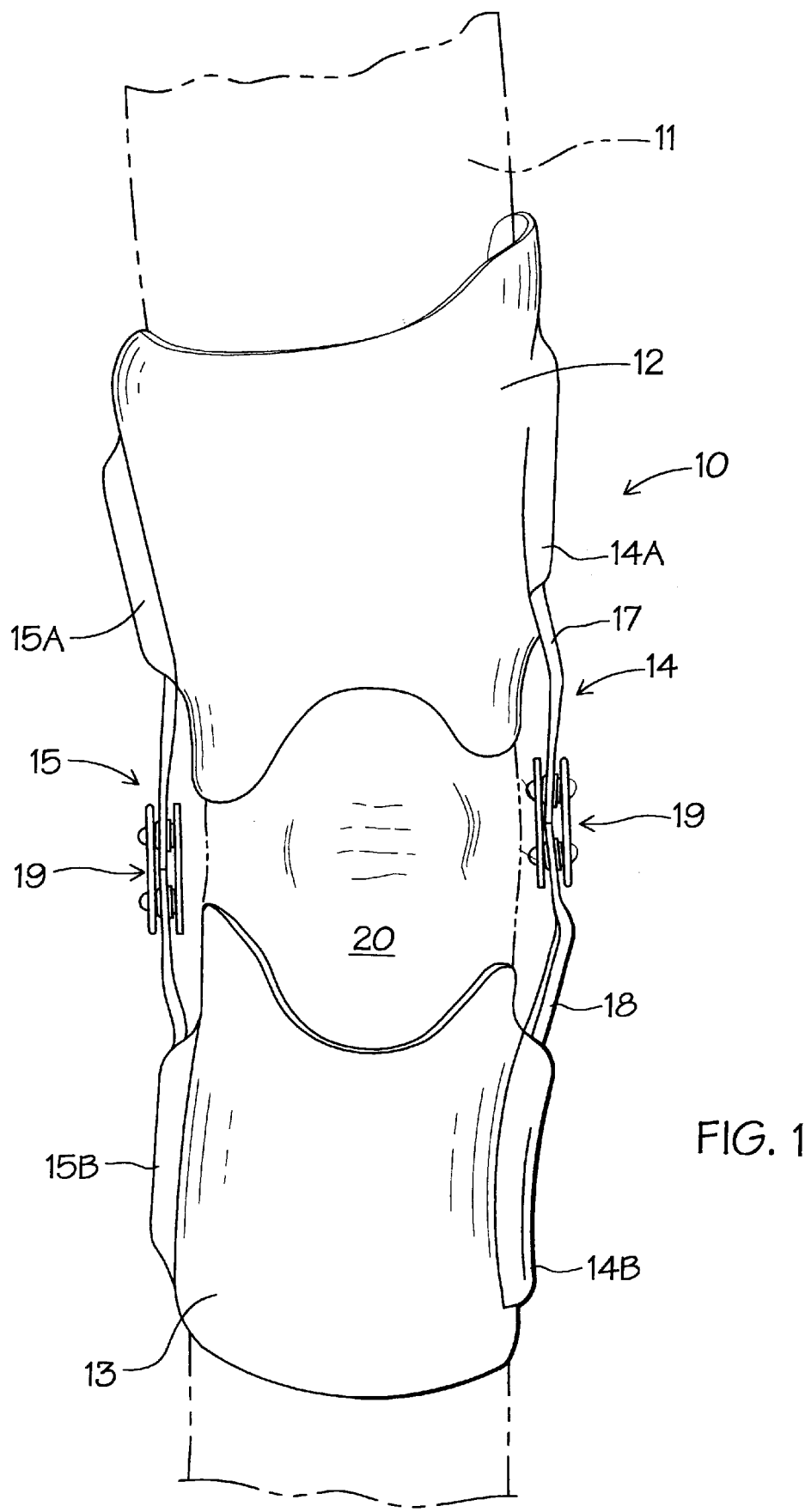
FIG. 1 is a front view of the orthopedic brace of the invention.

Referring to FIG. 1 of the drawings, a knee brace 10 of the invention can be seen in which ancillary straps and fittings used to attach the brace 10 to the patient's leg 11, shown in broken lines, are not illustrated for clarity purposes.

The brace 10 has a contoured thigh upper engagement cuff 12 and a corresponding lower calf engagement cuff 13. In this example, chosen for illustration, a pair of bi-lateral support arm assemblies 14 and 15 extend from the thigh cuff 12 to the calf cuff 13. The support arm assemblies 14 and 15 are secured to the respective cuffs 14 and 15 by engagement within molded support pockets 14A & 14B and 15A & 15B formed on the exterior surfaces of the respective cuffs 12 and 13 as will be described in greater detail hereinafter.

Each of the support arm assemblies 14 and 15 have an upper support arm 17 and a lower support arm 18 interconnected by a pivotal joint 19 that allows for bending of an anatomical knee 20 of the wearers leg 11, shown in broken lines.

Figure 2:
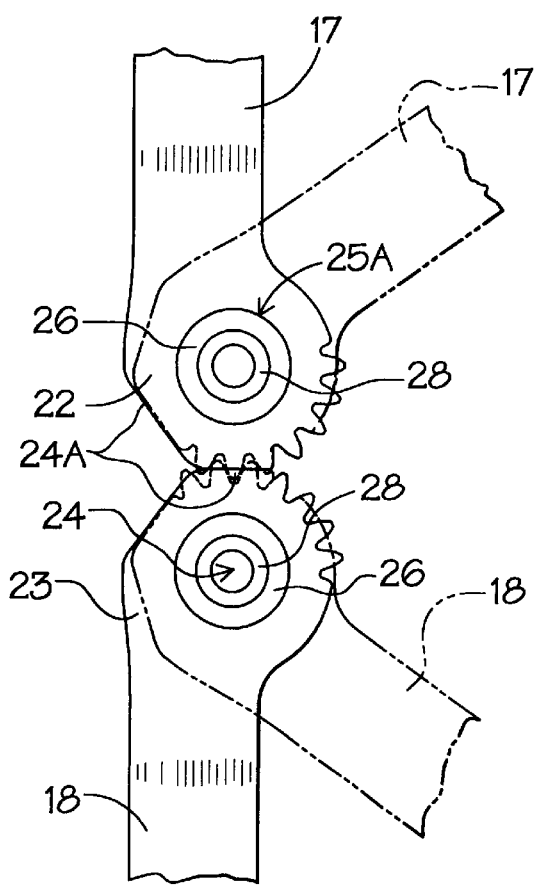
FIG. 2 is a partial side elevational view of a bi-pivotal brace joint with portions removed for clarity.

The pivotal joint 19 is defined as a self-aligning polycentric joint that will allow stress to be imparted to the anatomical knee 20 into various valgus or varus positions as is required for therapeutic treatment within the art. The upper support arms 17 are formed with an apertured geared end portion 22, best seen in FIG. 2 of the drawings. The lower support arms 18 correspondingly have an apertured geared end engagement portion 23 that upon joint rotation about a pivot point 24 meshes with the hereinbefore described geared end portion 22 as illustrated in broken lines. Each of the respective gear end portions 22 and 23 have a flat "stop" surface at 24A that upon rotation engagement limits the respective arm rotation as will be well understood by those skilled in the art.

Figure 5:
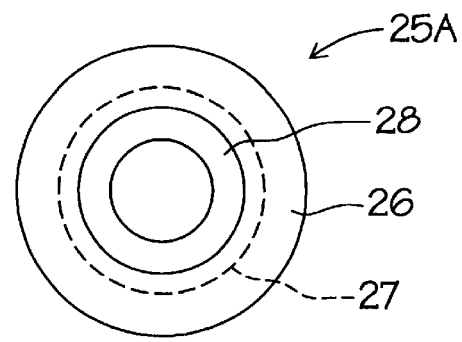
FIG. 5 is an enlarged side-elevational view of the polycentric joint component insert removed from the respective support arms.
Figure 4:
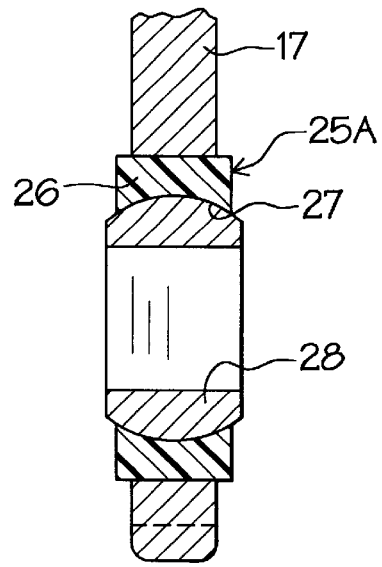
FIG. 4 is an enlarged cross-sectional view of a polycentric joint within each of the respective support arms.

A polycentric joint assembly 25 has a joint insert 25A that is secured within the apertures of the respective upper and lower support arms 17 and 18. The polycentric joint insert 25A as best seen in FIGS. 4 and 5 of the drawings has a synthetic retaining bushing 26 with an annular concave seat 27 within. An apertured spherical bearing element 28 is freely rotatable within the seat 27. A pair of apertured joining plates 29 and 30 interconnect the respective upper and lower support arms 17 and 18 with threaded fasteners 31 and 32 that extend through respective longitudinally spaced apertures at 29A and 29B in the plate 29 and threaded apertures 30A and 30B in the plate 30. It will be apparent that retaining bushing 26 can also be made of non-synthetic material.

Figure 3:
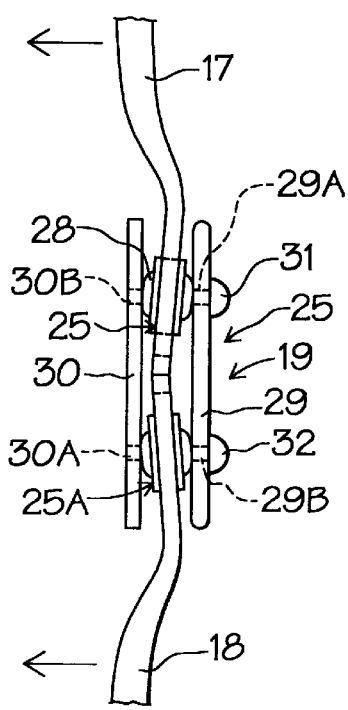
FIG. 3 is a front elevational view of the joint portion of the brace illustrating maximum angular inclination of the respective support arms to one another in the joint.
Figure 3A:
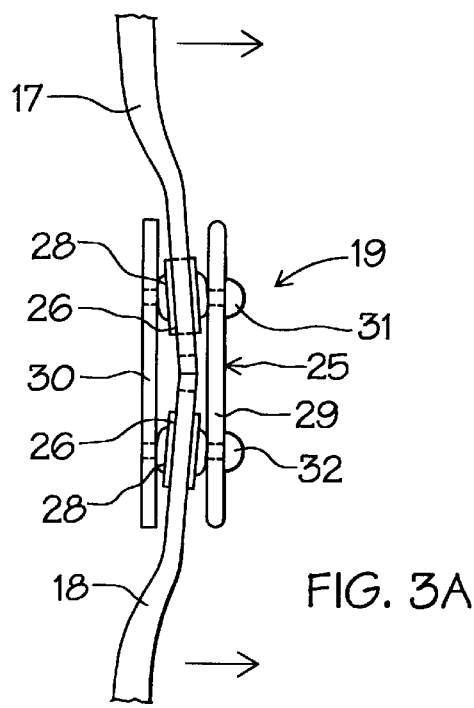
FIG. 3A is a front elevational view of the joint shown in FIG. 3 illustrating opposite maximum angular inclination of the support arms exaggerated for clarity.

The fasteners 31 and 32 extends through the respective bearing elements 28 as best seen in FIGS. 3 and 3A of the drawings and are threadably secured to the respective threaded apertures 30A and 30B. It will be evident from the above description that the polycentric joint inserts 25A will allow for angular inclination between the upper and lower arms 17 and 18 to be imparted thereto within the transverse limitation imposed by the respective space between the plates 29 and 30 as illustrated graphically.

It will also be seen that even at the maximum imparted angular inclination of the arms 17 and 18 illustrated within the joint assembly 25 of the invention will still maintain a non-binding engagement between the geared end portions 22 and 23 during extension and flexation of the anatomical knee joint 20.

Figure 6:
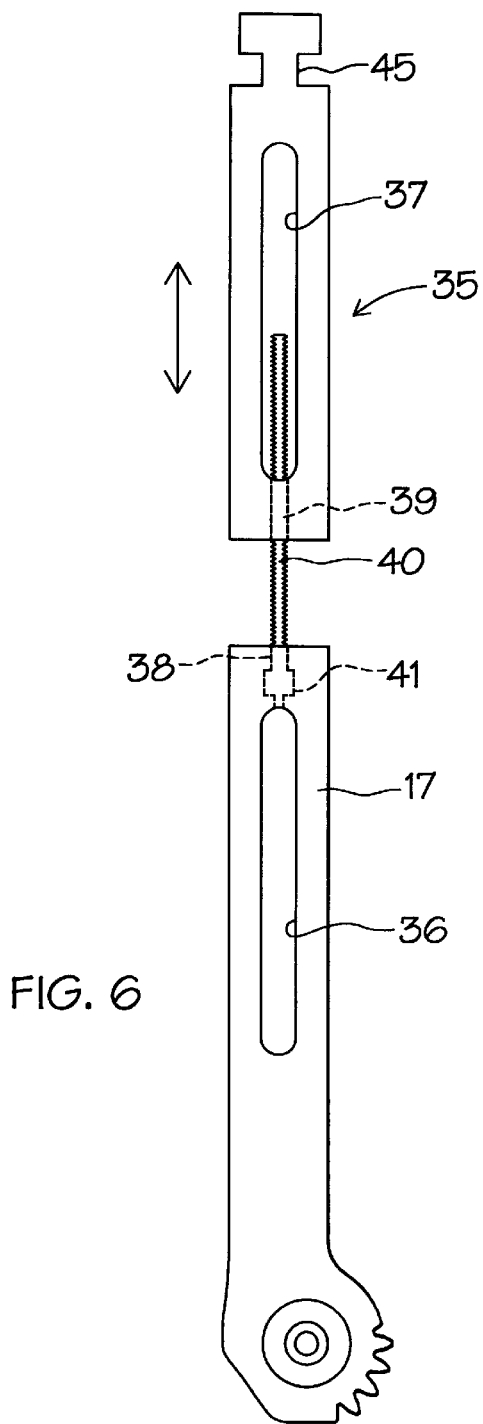
FIG. 6 is a side elevational view of a linear adjustable support arm of the invention.
Figure 7:
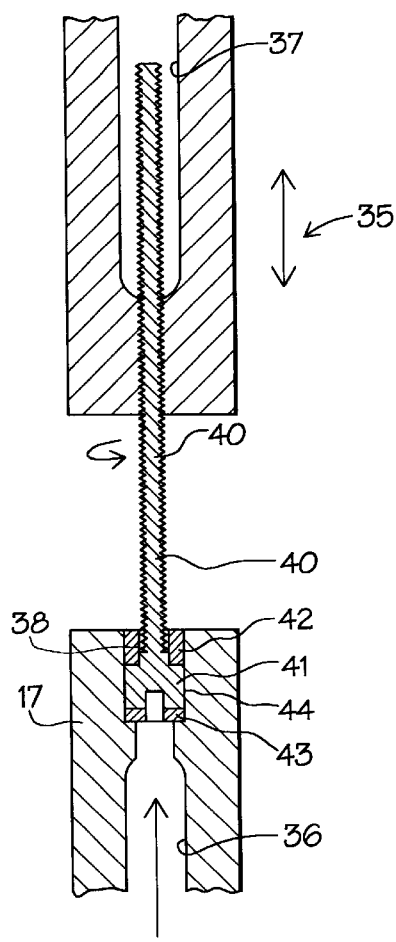
FIG. 7 is an enlarged partial cross-sectional view of the linear adjustment assembly of each support arm.

Referring now to FIGS. 6 and 7 of the drawings, the support arm 17 is shown having a linear length adjustment portion 35 adjustably secured to the proximal end of the arm 17. The support arm 17 and adjustment portion 35 have elongated arcuate slots at 36 and 37 respectively within and bores 38 and 39 axially extending within respectively. An elongated adjustment screw 40 extends through the bore 38 and rotatably retained by its head 41 between a pair of synthetic retaining bushings 42 and 43 and an enlarged area 44 of the bore 38 in the support arm 17 as best seen in FIG. 7 of the drawings. The screw 40 is threadably engaged through the bore 39. Accordingly, the overall affected length of the support arms 14 and 15 can be adjusted by rotation of the screw 40 via the slot 36 advancing or retracting the arm portion 17 with respect to the linear length adjustment portion 35 which is secured to the cuff 12 by anchor notches 45 in its free ends. By selectively adjusting the length of the respective arms, the angle of inclination is imparted to the brace 10. The pivot joint inserts 25A which are in spaced relation to the engagement of the respective geared end portions 22 and 23 allow for angular inclination relative one another, best seen in FIGS. 3 and 3A of the drawings.

It will be apparent that the arms 18 may also be "linearly" adjusted by identical adjustment portions 35 so that a variety of input angular inclinations may be achieved by different adjustment position selection of arm incremental sections.

Figure 8:
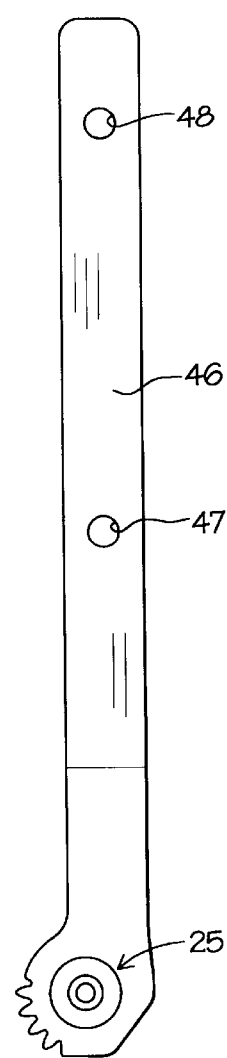
FIG. 8 is a side elevational view of an alternate support arm having a fixed non-adjustable configuration.
Figure 9:
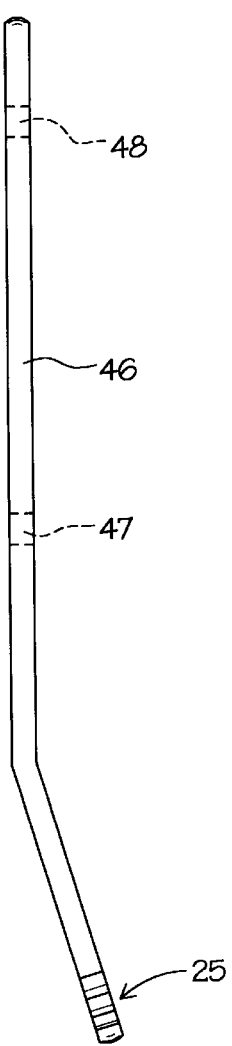
FIG. 9 is a front view of an alternate support arm as seen in FIG. 9 of the drawings.

Referring now to FIGS. 8 and 9 of the drawings, a fixed support arm element 46 can be seen without any linear adjustment feature to be used with the pivot joint assembly 25 as hereinbefore described. This support arm 46 can be used to oppose the linear adjustable support arm joints to create a fulcrum which when it is needed in selected brace configuration venues while maintaining normal flexation of the anatomical joint. Mounting apertures 47 and 48 allow the support arm elements 46 to be directly mounted to the surface of the leg engagement cuffs 12 and 13 that are so modified to be without the hereinbefore described pockets 14A and 15A. Alternately, the fixed support arms 46 with the pivot joint assembly 25 when used as both medial and lateral joints on a knee orthosis, it will provide anterior/posterior and medial/lateral stability for the applied anatomical joint while still providing a non-binding smooth anatomical joint motion with optimal support.

Referring back to FIG. 1 of the drawings, the arm engagement pockets 15A and 15B and 14A and 14B are shown in this illustrated application so as to support and confine the ends of the respective arms 17 and 18 within the confines of the pockets. In the linearly adjustable application set forth here and above, the adjustment portion 35 is secured by molding or bonding within the respective pocket portion so as to be fixed allowing the respective arm portion 17 to be slideably adjustable by advancement of the hereinbefore described adjustment screw 40 thus imparting the linear adjustability to the respective arm assemblies as noted.

It will therefore be apparent to those skilled in the art that various changes and modifications may be made therein without departing from the spirit of the invention, therefore.

I claim:

1. An orthopedic brace comprising a pair of bi-lateral support arm pairs secured to a wearers body, a compound pivot joint interconnecting the arm pairs to allow bending of an anatomical joint, means for imparting selective angular inclination to said support arms at their point of mutual engagement, said pivot joint comprises a first polycentric joint insert in one of said arms of said arm pairs, a second polycentric joint insert in said remaining arm of said arm pairs, apertured joint support plates extending between said first and second polycentric joint inserts, fastening means interconnecting said support plates through said respective polycentric joint inserts, means for limiting said bending of said anatomical joint at said arm's point of mutual engagement, means for securing said arm pairs to said wearers body.

2. The brace set forth in claim 1 wherein said polycentric joint inserts comprises, a retaining bushing in said arm pairs, an apertured polycentric bearing element rotatably positioned within said retaining bushing.

3. The orthotic brace set forth in claim 1 wherein said polycentric joint inserts are positioned in said respective arm pairs adjacent said point of mutual attachment.

4. The orthopedic brace set forth in claim 1 wherein said means for imparting selective angular inclination to said support arms comprises, a linearly adjustable arm length portion threadably secured to said respective arm pairs in oppositely disposed relation to said compound pivot joint.

5. The orthopedic brace set forth in claim 4 wherein said linear adjustment arm length portion comprises, an elongated body member, a slot within said body member, a threaded bearing bore extending through said body member from said slot.

6. The orthopedic brace set forth in claim 4 wherein said means for imparting selective angular inclination to said support arms further comprises, an elongated access opening in said arm parts adjacent its proximal end, a threaded fastener extending longitudinally from said opening threadably engaged in said threaded bore of said elongated body member, means for retaining said fasteners in said respective arms.

7. The orthopedic brace set forth in claim 6 wherein said means for retaining said fasteners in said respective arm portions comprises, a retaining chamber, bushings registerable with said fastener in said retaining chamber and a bore in communication with said chamber.

8. The orthopedic brace set forth in claim 1 wherein said means for securing said respective arm pairs to said wearers body comprises, contoured engagement cuffs.

9. The orthopedic brace set forth in claim 8 wherein said engagement cuffs are made of synthetic resin material.

10. The orthopedic brace set forth in claim 8 wherein said means for securing respective arm pairs to said wearers body further comprises opposing anchor notches in said respective engagement body members proximal free ends.

11. An orthopedic brace comprising, a pair of bi-lateral support arm pairs secured to a wearers body, each of said arm pairs having an upper arm and a lower arm, a compound pivot joint interconnecting said upper and lower arms, a geared head portion on each of said arms within said compound joint for meshed engagement with one another, a bore extending longitudinally inwardly from said arm's distal ends, a linear adjustment fitting threadably connected to one of said arms and means for securing said arm pairs to said wearers body.

12. The orthopedic brace set forth in claim 11 wherein said compound pivot joint comprises, polycentric joint inserts in said respective arms, support plates extending between said respective joint inserts, fastenening means interengaging said support plates through said joint inserts.

13. The orthopedic brace set forth in claim 11 wherein said arm pairs are secured to the wearer's body by contoured engagement cuffs on either side of an anatomical joint.

14. The orthopedic brace set forth in claim 11 wherein said means for securing said arm pairs to the wearers body comprises an adjustment arm length portion secured within said respective engagement cuffs, said arm pairs being movable axially within said respective engagement cuffs in respective relation to one another.

\* \* \* \* \*